United States Patent [19]

Bagros

[11] 4,387,094
[45] Jun. 7, 1983

[54] CONTRACEPTIVE METHOD AND COMPOSITION CONTAINING TANNIC ACID

[75] Inventor: Michel Bagros, Paris, France

[73] Assignee: Laboratories Human-Pharm S.A., Perret, France

[21] Appl. No.: 236,281

[22] Filed: Feb. 18, 1981

Related U.S. Application Data

[63] Continuation of Ser. No. 48,085, Jun. 13, 1979, abandoned, which is a continuation of Ser. No. 878,262, Feb. 18, 1978, abandoned, which is a continuation-in-part of Ser. No. 680,057, Apr. 26, 1976, abandoned.

[51] Int. Cl.³ .............................................. A61K 31/70
[52] U.S. Cl. .................................... 424/180; 424/319; 424/DIG. 14
[58] Field of Search ........ 424/195, 180, 319, DIG. 14

[56] References Cited

PUBLICATIONS

Physicians Desk Reference (PDR), 1968, p. 668.
Baker, J. of Hygiene, (Apr., 1932), pp. 171–183.
Merck Index, 9th ed., 1976, p. 229, Item 1807.

*Primary Examiner*—Leonard Schenkman
*Attorney, Agent, or Firm*—Dennison, Meserole, Pollack & Scheiner

[57] ABSTRACT

The present invention relates to a novel local contraceptive method according to which the passage of spermatozoa in the cervical canal is prevented, the said method being characterized in that the physico-chemical structure of the cervical mucus is modified by means of at least one coagulating agent. It also concerns compositions for putting this novel method into effect, particularly compositions comprising at least one coagulating agent such as tannic acid. These compositions may also contain an agent which assists and completes the action of the coagulating agent.

2 Claims, No Drawings

CONTRACEPTIVE METHOD AND COMPOSITION CONTAINING TANNIC ACID

This is a continuation of application Ser. No. 048,085, filed June 13, 1979, now abandoned; which is a continuation of application Ser. No. 878,262, filed Feb. 18, 1978, now abandoned, which is a continuation-in-part of application Ser. No. 680,057, filed Apr. 26, 1976, now abandoned.

The present invention concerns a novel contraceptive method based on a modification of the structure of the cervical mucus. It also concerns the means by which the said method can be carried out.

It is known that, to prevent fertilisation of the ovule, apart from contraception by hormones, mechanical means and chemical means involving spermicidal compositions have already been suggested; each of these methods has its disadvantages, its risks and its limitations.

It is also known that, to reduce the risks, to improve the reliablity and to make the use easier, local contraceptives have more recently been proposed which are soluble or capable of melting in the vagina in such a manner as to release the spermicide or spermicides which they contain. None of these methods is entirely reliable.

According to the invention, to solve the technical difficulties of local contraception, a novel solution is suggested, differing from the solutions envisaged in the prior art. The local contraceptive method now proposed is based on the discovery that the structure of the cervical mucus (also called cervical glair) can be modified so as to provide a barrier, a physico-chemical obstacle preventing the ascent of spermatozoa.

The following should be remembered in order to understand properly the basic idea which is the origin of the invention.

In the entire course of the menstrual cycle, the mouth of the cervical canal is the source of a mucus secretion. At the moment of ovulation, the mucus substances (the cervical mucus) completely occupies the space which must necessarily be crossed by the spermatozoa during the whole of the period preceding and accompanying the presence of a fertilizable ovule in the neighbourhood. The function of the cervical mucus is to gather together the spermatozoa, to select the most active of them and to put these in reserve in the best conditions of protection and conservation and, finally, to guide them progressively towards the uterine cavity.

The production of the cervical mucus is considerably increased at the stage immediately preceding ovulation: the amount of cervical mucus normally secreted is from 20 to 60 mg. per 24 hours but can rise to 700 mg, per 24 hours at the pre-ovulatory stage.

The cervical mucus is a thread-like, viscous, elastic and adhesive substance; it contains 92 to 95% of water normally and up to 98% by weight of water at the time of ovulation. Apart from the water, mineral salts (especially sodium chloride), sugars (particularly glucose, maltose and mannose), amino-acids and enzymes, the most important components of the cervical mucus are proteins, more particularly glycoproteins which enter into the composition of mucin.

The mucin, the amount of which increases at ovulation, is composed of glycoprotein macromolecules which (a) comprise long protein chains (fibrils) which are more or less parallel with each other and possess polysaccharide side chains terminated by sialic acid functional groups and (b) are polymerised, the cohesion of the whole arising from non-covalent bonding forces and by disulphide bridges between the protein fibrils. These bridges form, with the fibrils, a three-dimensional network through which can circulate the liquid phases in the cervical canal. It is this three-dimensional network that permits the penetration and progression of the spermatozoa.

It has been found that the size of the openings in the network varies considerably under the influence of the ovarian hormones during the course of a cycle: the openings enlarge during the ovulation stage, forming channels, or dies, guiding the progress of the spermatozoa towards the uterus; outside this stage the openings shrink, especially during the luteal stage, thus resisting the passage of spermatozoa. During the ovulation stage, in the cervical mucus from 100 to 1000 glycoprotein chains can be counted, the size of these chains being 0.5 microns and each chain being situated 3 microns distant from another.

To put the invention into effect, the three-dimensional network is destroyed so as to oppose upward movement of spermatozoa, in particular by a modification of the structure and consistency of the cervical mucus which renders the latter impassable to spermatozoa. The means used according to the invention to effect the modification is coagulation.

The contraceptive method of the invention, according to which the passage of spermatozoa into the cervical canal is prevented, is characterised in that the physico-chemical structure of the cervical mucus is modified by use of at least one coagulating agent.

According to the invention there is provided a composition containing, in association with a physiologically acceptable excipient, at least one agent which modifies the physico-chemical structure of cervical mucus, namely a coagulating agent.

According to a second aspect of the invention the composition contains at least one coagulating agent and at least one spermicidal agent. It also permits the presence of at least one agent which assists and completes the action of the coagulant on the mucus.

Amongst suitable coagulants, the following in particular may be mentioned:

tannin, its constituents and its derivatives such as for example gallic, ellagic, luteolic and digallic acids and their esters, especially the esters with sugars, particularly penta-(digalloyl)-glucose, penta-galloyl-glucose,α-glucogalline and β-glucogalline;

polyphenols, particularly those belonging to the resorcinol group and derivatives thereof;

benzoic acid;

metal thiosulphates, especially sodium thiosulphate;

flavianic acid and its derivatives; and cetyltrimethylammonium chloride and bromide.

The preferred coagulants are officinal tannin (also termed "tannic acid" and "ether tannin") and its chief constituent which corresponds to the name penta-(digalloyl)-glucose. These substances coagulate proteins very efficiently and, in particular, mucin, are of low toxicity and tolerated well by the organism (they are especially well tolerated when administered by the buccal route at a daily dose of up to 4 g. and are also endowed with antiseptic properties.

Amongst the adjuvants which assist and complete the effect of the coagulating agent, there may be mentioned:

carboxymethylcysteine;

substances having a local immunological effect (by use of antibodies formed in situ), for example human anti-protein serums, anti-follicular and anti-ovular substances, anti-spermatozoa antibodies and blood antigroup substances (by reason of the marked analogy of the latter substances with mucin);

substances which block SH groups, for examples quinones;

enzymatic substances which degrade the cervical mucus or homogenise the mucus and the other ingredients contained in the composition according to the invention, for example pepsin, trypsin, papain, mucinase, mucopolysacchardiase, neuraminidase, lysozyme, bromelain and hyaluronidase (the last two enzymes can advantageously be used as homogenising agents);

acids, in particular lactic, citric, acetic; boric, sulfosalicyclic and acetylsalicylic acids;

fluidifying substances, such as sodium benzoate.

The degradation of the cervical mucus by means of an enzymatic agent is thought to assist the action of the coagulating agent, and to prevent that action being limited simply to a surface effect. In fact, proteolysis of cervical mucus reduces its viscosity, modifes the properties of the colloidal gel, even the fibrillar structure of the glycoprotein molecules. Thus, the action of the coagulating agent, properly so called, is prepared for by a good distribution in the mass of the cervical mucus. It is indeed important that the attack should be total, massive and rapid. The spermatozoa then find themselves in fact enveloped in the midst of a coagulated medium which holds them in place.

Carboxymethylcysteine is one of the preferred adjuvants that may be included in a composition according to the invention together with the coagulating agent; in fact this substance acts on the disulphide bridges of the three-dimensional network. The result of this action is a mucolysis. The carboxymethylcysteine alters the structure of the cervical mucus and thus completes the effect of the coagulating agent. Apart from its action on the disulphide bridges, this substance also possesses a coagulating effect on the mucus and an immobilizing effect on spermatozoa.

It is possible that the compositions according to the invention contain one or several spermicidal agents such as benzethonium chloride, cetylpyridinium chloride, benzalkonium chloride, p-nonylphenoxy(ethoxy)$_n$-ethanol(where n is an integer, especially 9), phenylmercury nitrate and vanillylidene-bis-thioacetic acid.

In fact it has been found that the presence of one spermicidal agent is not necessary when carrying out the best mode of this invention which consists in administering a composition containing tannic acid, as coagulating agent, and carboxymethylcysteine as adjuvant for assisting and completing the effect of the coagulating agent.

The composition according to the invention which, in practice, is preferred for the local contraceptive method is characterised in that it comprises:

(a) 30 to 80 parts by weight of at least one coagulating agent selected from the group consisting of:

tannin its components and its derivatives (especially gallic, ellagin, luteolic and digallic acids and their esters, especially penta-digalloyl)-glucose, pentagalloyl-glucose,α-glucogalline and β-glucogalline);

polyphenols, especially those of the resorcinol group and derivatives thereof;

benzoic acid;

flavianic acid and its derivatives; and cetyltrimethylammonium chloride and bromide, (b) an effective amount of at least one agent that assists and completes the effect of the coagulating agent.

An example of a suitable composition contains, in association with a physiologically acceptable excipient:

(a) 30 to 80 parts by weight of tannic acid, and (b) 0.5 to 10 parts by weight of carboxymethylcysteine.

When a spermicidal agent is used, the preferred amount is comprised between 10 and 50 parts by weight of such an agent, for instance benzalkonium chloride or phenylmercury nitrate. But as said before the presence of a spermicidal agent is not necessary with respect to the success of the local contraceptive method.

To achieve the object of the invention, i.e. to provide an effective local contraceptive action, the composition according to the invention should be placed at the base of the vaginal cavity near the uterine neck or on the latter. The application can be effected manually or by means of an applicator. The application should be effected before sexual intercourse. Once the cervical mucus has been coagulated, contraceptive protection remains assured for as long as the coagulum is not eliminated, in particular by the pressure of a flow of secretions. Although the protection can last several hours, even several days, it is always wise to provide for administration of the composition according to the invention at least once a day in the form of a unit dose. It can be formulated in slow acting forms so as to prolong the protection.

The composition should be provided in a form best suited to facilitate its introduction into the desired position. For this reason it is appropriate that all the forms should be suited for vaginal application and for subsequent release of the active ingredients; examples of suitable forms are compressed tablets, soft suppositories, pastes, emulsions, either free or carried on a support or dissociable in the medium, or aerosols.

The excipients which are suitable for these forms should be fusible at body temperature, or soluble in the vaginal medium or have both these properties or be dissociable in situ. Furthermore, they should not be incompatible with the active ingredients. Thus, for making soft suppositories, in particular there can be used glycerides, (for example glycerides obtained by esterification of hydrogenated vegetable oils and commercially available under the name "Suppocire"), glycerine solidified by means of gelatin according to the formulation in the French Pharmacopoeia, cocoa butter, ethoxylanolin, condensation products of ethylene oxide and/or propylene oxide, polyvinyl alcohol or mixtures of two or more such substances. To prepare compressed tablets and aerosols, the excipients usually employed for such purposes may be used, for example lactose, sodium carboxymethylcellulose, soluble starch, sodium bicarbonate and lubricants such as stearic acid and its salts, citric acid and sodium laurylsulphate.

Finally, it is possible to use the above-mentioned excipients together with a known pharmaceutical preservative for example methyl and ethyl p-hydroxybenzoates, an inert carrier (for example a powdery carrier which, by its incorporation, gives the resultant compositions a drier touch and makes it easier to manipulate), a colorant and a perfume.

It may also be noted that the composition according to the invention can be used in the treatment and prevention of infectious disorders of the female genito-urinary tract and, in particular, in the treatment and prevention of disorders induced by bacteria. In fact, it has been ascertained that the coagulating agent prevents the passage of mono-cellular micro-organisms through the cervical canal in the same way that it prevents that of spermatozoa. Accordingly, in the case of patients infected with pyogenic germs (especially gonococcus) the development of an ascending infection (metritic or salpingitic) can be prevented by "insulating" the uterus from the vagina by coagulation of the cervical mucus.

Other advantages and characteristics of the invention will be better understood by reference to the following examples of formulations which are non-limitative but are given by way of illustration. In the examples, the amounts are expressed in "parts by weight," the dose to be administered being one that provides sufficient activity.

EXAMPLE 1

| Formulation for soft suppositories | |
|---|---|
| Ether tannin | 70 parts |
| Benzalkonium chloride | 28 parts |
| Carboxymethylcysteine | 2 parts |
| Excipient (triglycerides of fatty acids), in a sufficient amount. | |

EXAMPLE 2

| Formulation for suppositories | |
|---|---|
| Tannic acid | 30 parts |
| Resorcinol | 36 parts |
| Benzalkonium chloride | 33 parts |
| Carboxymethylcysteine | 1 part |
| Excipient in a sufficient amount | |

EXAMPLE 3

| Formulation for compressed vaginal tablets | |
|---|---|
| Penta(digalloyl)-glucose | 50 parts |
| Cetyltrimethylammonium chloride | 30 parts |
| Phenylmercury nitrate | 20 parts |
| Excipient in a sufficient amount | |

EXAMPLE 4

| Formulation for effervescent compressed vaginal tablets | |
|---|---|
| Tannic acid | 65 parts |
| Cetylpyridinium chloride | 30 parts |
| Trypsin | 5 parts |
| Excipient for effervescent compressed tablets in a sufficient amount | |

Note
trypsin having a content of the order of 10,000 to 50,000 Anson units/mg. may be used.

EXAMPLE 5

| Formulation for an aerosol | |
|---|---|
| Tannin | 40 parts |
| Benzalkonium chloride | 50 parts |
| Carboxymethylcysteine | 10 parts |
| Excipient (propellant) in a sufficient amount | |

EXAMPLE 6

| Formulation for an aerosol foam | |
|---|---|
| Penta-(digalloyl)-glucose | 80 parts |
| Phenylmercury nitrate | 15 parts |
| Trypsin | 5 parts |
| Excipient (water, propellant, polysorbate - emulsified) in a sufficient amount | |

Note
trypsin having a content a content of the order of 10,000 to 50,000 Anson units/mg. may be used.

EXAMPLE 7

| Formulation for slow release suppositories | |
|---|---|
| First layer: | |
| Tannic acid | 33 parts |
| Benzalkonium chloride | 16 parts |
| Carboxymethylcysteine | 1 part |
| Triglycerides of fatty acids and other excipients, in a sufficient amount | |
| Second layer: | |
| Tannic acid | 33 parts |
| Benzalkonium chloride | 16 parts |
| Carboxymethylcysteine | 1 part |
| Polysorbate and other excipients in a sufficient amount | |

The following example is concerned with the preferred formulation according to the invention, that is to say the formulation used for carrying out the best mode.

EXAMPLE 8

| Formulation for vaginal tablets | |
|---|---|
| Tannic acid | 120 parts |
| Carboxymethylcysteine | 3 parts |
| Excipient in a sufficient amount in order to complete to 1000 parts. | |

According to the formulation of example 8 vaginal tablets of 1 g each were obtained. The average composition of each tablet being as follows:

| COMPOSITION I (for a tablet of 1000 mg) | |
|---|---|
| Tannic acid | 120 mg |
| Carboxymethylcysteine | 3 mg |
| Lactose | 507 mg |
| Sodium bicarbonate | 97 mg |
| Citric acid | 203 mg |
| Hydroxypropylcellulose | 40 mg |
| Magnesium stearate | 20 mg |
| Talc | 10 mg |

The results of assays carried out on animals and women with tablets according to composition 1, have been summarized hereinafter. The animals were treated with a solution (called "solution A") obtained from the dissolution of 1 tablet in 10 ml of distilled water.

1—TOXICITY

Ten female mice (of Swiss race, weighing each 20 g) received per os (through a gastric probe) a daily dose of 1 ml of A for 20 g of body weight. After a treatment of 7 days no death was reported (i.e. the LD - O of composition I is higher than 5 g/kg).

2—VAGINAL TOLERANCE

Solution A was administered (vaginal application) to female animals. Five female rabbits received each a daily dose of 0.05 ml of solution A for 14 days, two female rabbits, taken as control animals, receiving only a daily dose of 0.05 ml of an aqueous solution containing 9 g/l of NaCl. Ten female rats received each a daily dose of 0.05 ml of solution A for 8 days, eight female rats, taken as control animals, receiving only a daily dose of 0.05 ml of water containing 9 g/l of NaCl.

After slaughter of the rabbits and rats, the autopsy of the urogenital tracts showed no sign of irritation.

3—CLINICAL ASSAYS

Volunteer women were selected according to the following criteria:
(i) they were in child bearing years,
(ii) they had no previous past record of possible sterility,
(iii) during the treatment they agreed to have intercourse at least once a week, not to use any other contraceptive method, and not to have any other local gynecological treatment.

A first experiment carried out on a group of 10 women (aged from 20 to 40 years, having a cycle of 24 to 40 days and having menses of 3 to 7 days) receiving 1 to 2 vaginal tablets according to composition I each 1,2 or 4 days during a period of two weeks, pointed out that the coagulation of the cervical mucus was total within 15 minutes at most more precisely within 5–15 minutes, after administration, and that the duration of the effect of one tablet was of 15 to 18 hours.

A second experiment carried out on the very same group of 10 women receiving 1 vaginal tablet according to composition I before sexual intercourse for 6 months (i) showed no irritation for both the women and their partners, and (ii) no pregnancy occurred.

These two experiments teach that the best mode to carry out the local contraceptive method according to the invention, consists in administering to women in need of such a treatment an effective amount of tannic acid (preferably 120 mg) and of carboxymethylcysteine (preferably 3 mg) before sexual intercourse.

I claim:

1. A contraceptive method which essentially comprises administering vaginally prior to sexual intercourse an amount of a composition comprising as essential constituents tannic acid and as an adjuvant carboxymethylcysteine in amounts effective to prevent the passage of spermatozoa along the cervical canal to the uterine cavity by coagulation of the cervical mucus for rendering the mucus impassable to spermatozoa, said composition comprising on the basis of weight:
   about 30 parts to about 80 parts tannic acid; and
   about 0.5 parts to about 10 parts carboxymethylcysteine.

2. A contraceptive composition for vaginal administration prior to sexual intercourse and comprising a physiologically acceptable carrier and a cervical mucus coagulant essentially comprising tannic acid and as an adjuvant carboxymethylcysteine present in amounts effective in use to prevent passage of spermatozoa along the cervical canal to the uterine cavity by rendering the mucus impassable to spermatozoa, said comprising on the basis of weight:
   about 30 parts to about 80 parts tannic acid; and about 0.5 parts to about 10 parts carboxymethylcysteine.

* * * * *